United States Patent
Nogami et al.

(10) Patent No.: US 8,730,459 B2
(45) Date of Patent: May 20, 2014

(54) EXAMINATION DEVICE AND EXAMINATION METHOD

(75) Inventors: Makoto Nogami, Tsuchiura (JP);
Katsuhiro Kanda, Hitachinaka (JP);
Shinya Ito, Hitachinaka (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 59 days.

(21) Appl. No.: 13/501,941

(22) PCT Filed: Oct. 15, 2010

(86) PCT No.: PCT/JP2010/068173
§ 371 (c)(1),
(2), (4) Date: May 3, 2012

(87) PCT Pub. No.: WO2011/046207
PCT Pub. Date: Apr. 21, 2011

(65) Prior Publication Data
US 2012/0206713 A1  Aug. 16, 2012

(30) Foreign Application Priority Data
Oct. 16, 2009  (JP) ................. 2009-239236

(51) Int. Cl.
*G01N 33/48*  (2006.01)
(52) U.S. Cl.
USPC ............................................. 356/39; 356/42

(58) Field of Classification Search
USPC .......... 356/39–42; 422/935, 44–48; 436/174, 436/177, 180, 8; 210/473, 477, 479
See application file for complete search history.

(56) References Cited

U.S. PATENT DOCUMENTS

| | | | |
|---|---|---|---|
| 6,788,937 | B1 | 9/2004 | Willenegger et al. |
| 6,878,343 | B2 | 4/2005 | Sklar et al. |
| 2002/0119576 | A1 | 8/2002 | Sklar et al. |
| 2006/0008922 | A1 | 1/2006 | Chace |

FOREIGN PATENT DOCUMENTS

| | | |
|---|---|---|
| JP | 04-208856 A | 7/1992 |
| JP | 2001-013151 A | 1/2001 |
| JP | 2002-504693 A | 2/2002 |
| JP | 2006-308411 A | 9/2006 |

*Primary Examiner* — Tri T Ton
(74) *Attorney, Agent, or Firm* — Mattingly & Malur, PC

(57) ABSTRACT

Provided herein are an examination device and an examination method that can efficiently perform examination even when both whole blood and serum/blood plasma specimens are to be examined. A solid-phase extraction cartridge or a filter is placed on a continuous track of a cartridge table. A cup table is disposed below the cartridge table. A cup is placed on a continuous track of the cup table to receive a sample purified by the filter. When viewed from above, the continuous track of the cartridge table and the continuous track of the cup table cross each other at a position "m", and each of the tracks crosses a position at which a sample probe operates. A pretreatment for serum/blood plasma is completed in one rotation of the cartridge table. A pretreatment for whole blood is completed in two rotations of the cartridge table.

6 Claims, 13 Drawing Sheets

FIG. 3

| PROCESS NUMBER | PRETREATMENT OF SERUM/BLOOD PLASMA | WHOLE BLOOD | |
|---|---|---|---|
| 1 | a; TRANSPORT CARTRIDGE | a; TRANSPORT FILTER | FIRST HALF |
| 2 | b; ADD METHANOL | f; ADD SAMPLE | |
| 3 | c; APPLY PRESSURE | g; ADD INTERNAL STANDARD SUBSTANCE | |
| 4 | d; ADD WATER | h; ADD ZINC SULFATE AQUEOUS SOLUTION | |
| 5 | e; APPLY PRESSURE | l; ADD METHANOL | |
| 6 | f; ADD SAMPLE | m; APPLY PRESSURE | |
| 7 | g; ADD INTERNAL STANDARD SUBSTANCE | n; TRANSPORT FILTER | |
| 8 | h; ADD DILUTING FLUID AND STIR | a; TRANSPORT CARTRIDGE | SECOND HALF |
| 9 | i; APPLY PRESSURE | b; ADD METHANOL | |
| 10 | j; ADD WATER | c; APPLY PRESSURE | |
| 11 | k; APPLY PRESSURE | d; ADD WATER | |
| 12 | l; ADD METHANOL | e; APPLY PRESSURE | |
| 13 | m; APPLY PRESSURE | f; ADD SAMPLE | |
| 14 | n; DISCARD CARTRIDGE | i; APPLY PRESSURE | |
| 15 | | j; ADD WATER | |
| 16 | | k; APPLY PRESSURE | |
| 17 | | l; ADD METHANOL | |
| 18 | | m; APPLY PRESSURE | |
| 19 | | n; DISCARD CARTRIDGE | |

○: FOR SERUM/BLOOD PLASMA

●: FOR WHOLE BLOOD

◈: FOR URGENT EXAMINATION
(AVAILABLE PORT)

EXAMINATION DEVICE AND EXAMINATION METHOD

TECHNICAL FIELD

The present invention relates to examination devices and examination methods for testing biological samples such as blood by mass analysis, and more particularly to an examination device and an examination method that are provided with a pretreatment device for performing a pretreatment such as solid-phase extraction.

BACKGROUND ART

Immunoassay is an examination method widely used in clinical testing. On the other hand, analysis method by mass spectrometry (MS) is a measurement technique which measures target components based on the mass of the components. The sample can therefore be distinguished from molecules having a similar structure such as metabolites. Especially, MS/MS analysis and MSn analysis are technologies which allow distinction of components having similar structures with high accuracy by converting target components to fragment signals. Mass spectrometry analysis method excels in selectivity and accuracy compared to the immunoassay method, and a movement of applying it to clinical examination is spreading.

Mass spectrometry analysis method can be applied to clinical examinations such as therapeutic drug monitoring (TDM) and metabolic disorder screening. One example of TDM is observing pharmacokinetics of drugs in human body. For administration of drugs to patients in medical sites, it is important to plan a dosing plan based on the symptom of each patient in order to ensure effectiveness and safety. Even if patients take the same amount of drugs, their therapeutic effects may differ. One reason for this is that the blood concentration of the drug in patients differs due to individual differences in drug pharmacokinetics. Therefore, one performs TDM, a technique of optimizing the dosage amount and dosage method by measuring the patient's blood concentration, so that it falls within a therapeutic range. For example, TDM is necessarily performed for immunosuppressants used to suppress rejection response to a transplanted organ. The therapeutic range of those immunosuppressants is in a low concentration range, from several ng/mL to several hundred ng/mL. When the patient's blood concentration of a drug exceeds the therapeutic range, a severe side effect such as hypertension, hyperglycemia, a peptic ulcer, or dysfunction of the liver or kidney may occur. In order to reduce such side effects, cocktail administration is generally performed, in which multiple types of immunosuppressants and a drug such as a steroid are administered while performing TDM.

Another known example is metabolic disorder screening in which whole blood is used as a specimen, and target components are extracted by liquid-liquid extraction to be measured by a mass spectrometer (Patent Document 1). Amino acids such as alanine and valine, and acyl carnitine are thus quantitated so as to examine the degree of the metabolic reaction of the target component in vivo.

The MS mode employed in the aforementioned two examples is the multiple reaction monitoring (MRM) mode of a triple quadrupole mass spectrometer which has high selectivity. MRM is a technique such that the first stage quadrupole functions as a filter to pass only the precursor signal through it, and the passed signal is cleaved in a collision cell so that only a product signal that is specific to the generated compound is monitored in the second stage quadrupole. In this method, a compound is examined by identifying it using mass information specific to the compound.

On the other hand, regarding the series of operations performed in a clinical application of mass spectrometry, although the device automatically analyzes samples, pretreatment of the samples are performed manually. A laboratory technologist needs to conduct a plurality of pretreatment processes using a plurality of devices, resulting in low efficiency. Therefore, there is a demand for a device that can efficiently perform a series of examinations so as to save labor, shorten the time for examination reporting, and downsize the device by integrating the components.

The substance to be examined may exist in a blood cell component or a serum/blood plasma component, and the specimen may be whole blood or serum/blood plasma, because the position of localization varies depending on the property of the substance to be examined. A pretreatment for whole blood is different from that for serum/blood plasma. Therefore, a device that can handle various examination items, that is, various pretreatments is demanded.

As an example of a technique capable of performing pretreatments on both whole blood and serum/blood plasma, there is a known device that can consistently perform immunoserological examination or biochemical examination which uses serum as a specimen, and blood coagulation examination which uses whole blood as a specimen (refer to, for example, Patent Document 2). The device performs the first half process of the biochemical examination or immunoserological examination in parallel with the process of the blood coagulation examination on the same examination area so that two types of examinations are performed consistently and efficiently.

PRIOR ART DOCUMENTS

Patent Documents

Patent Document 1: US Patent Application No. 2006/0008922
Patent Document 2: JP-2001-13151-A

SUMMARY OF THE INVENTION

Problem to be Solved by the Invention

However, in the technique described in Patent Document 1, pretreatments need to be manually conducted.

Referring to the technique described in Patent Document 2, although the device is capable of performing the pretreatments for both whole blood and serum/blood plasma, it cannot handle pretreatments of clinical applications of mass spectrometry.

In addition, Patent Documents 1 and 2 both have a problem that the configuration of the device cannot be simplified, for example, to a configuration such that the device can perform all pretreatments on one disk.

An object of the present invention is to provide an examination device and an examination method which enable an efficient examination even for examinations using both whole blood and serum/blood plasma as specimens.

Means for Solving the Problem (1) In order to accomplish the aforementioned object, an aspect of the present invention provides an examination device comprising:

a cartridge table that can hold a solid-phase extraction cartridge and a filter on a continuous track;

a plurality of pressure applying units arranged above the cartridge table, the pressure applying units applying pressure to the inside of the solid-phase extraction cartridge and the inside of the filter;

a cup table disposed below the cartridge table, the cup table being able to hold a cup on a continuous track, where the cup receives a purified sample;

a sample probe for dispensing a sample into the solid-phase extraction cartridge and the filter;

a reagent probe for dispensing a reagent into the solid-phase extraction cartridge and the filter; and an analyzer for analyzing an eluate obtained by completing a pretreatment;

wherein a pretreatment of serum/blood plasma is completed in one rotation of the cartridge table, and a pretreatment of whole blood is completed in two rotations of the cartridge table.

This configuration enables examinations using both whole blood and serum/blood plasma specimens to be efficiently performed.

(2) In the examination device of (1), preferably, the continuous track of the cartridge table and the continuous track of the cup table cross each other at a first position when viewed from above;

the continuous track of the cup table and a locus on which the sample probe operates cross at a second position;

the cup on the cup table receives the eluate eluted from the filter on the cartridge table at the first position;

the sample probe aspirates the eluate from the cup at the second position; and the sample probe dispenses the eluate into a solid-phase extraction cartridge on the cartridge table.

(3) Preferably, the examination device of (2) further includes:

a water dispenser for adding water to a liquid contained in a solid-phase extraction cartridge at a plurality of positions on the cartridge table;

a methanol dispenser for adding methanol to a liquid contained in a solid-phase extraction cartridge at a plurality of positions on the cartridge table; and a reagent disk that holds a plurality of reagents, the reagent disk being disposed at a position where the reagent probe can operate;

wherein in the pretreatment for serum/blood plasma, an internal standard substance held by the reagent disk is added into a solid-phase extraction cartridge on the cartridge table; and in the pretreatment for whole blood, an internal standard substance held by the reagent disk is added into a filter on the cartridge table.

(4) In the examination device of (1), preferably, a total of 14 solid-phase extraction cartridges and/or filters can be set on the continuous track of the cartridge table.

(5) In the examination device of (1), preferably, each of the processes on the cartridge table is performed at constant time intervals.

(6) In the examination device of (1), preferably, the rotational center of the cup table is located at a position different from the rotational center of the cartridge table, and the sample probe and the pretreated sample introducing mechanism can access from above the cup table.

(7) In order to achieve the above object, another aspect of the present invention provides an examination method for pretreating serum/blood plasma and whole blood and analyzing eluates obtained by the pretreatment, comprising the steps of:

pretreating serum/blood plasma using a solid-phase extraction cartridge set on a cartridge table; and pretreating whole blood by filtering the whole blood using a filter set on the cartridge table, then receiving an eluate from the filter with a cup on a cup table, and then returning the eluate received by the cup to a solid-phase extraction cartridge set on the cartridge table.

The method enables examinations using both whole blood and serum/blood plasma specimens to be efficiently performed.

Effect of the Invention

According to the present invention, examinations in which both whole blood and serum/blood plasma specimens are used can be efficiently performed.

BRIEF DESCRIPTION OF THE DRAWINGS

FIG. 3 is a diagram illustrating pretreatments for serum/blood plasma and whole blood performed by the examination device according to the embodiment of the present invention.

MODE FOR CARRYING THE INVENTION

The configuration and operations of an examination device according to an embodiment of the present invention are described with reference to FIGS. 1 to 12. Here, as an example, described is a case where the examination device is a drug examination device that performs pretreatments on whole blood and serum/blood plasma and analyzes them by mass spectrometry analysis method.

First, the entire configuration of the examination device according to the embodiment of the present invention is described with reference to FIGS. 1 and 2.

Figure 1:
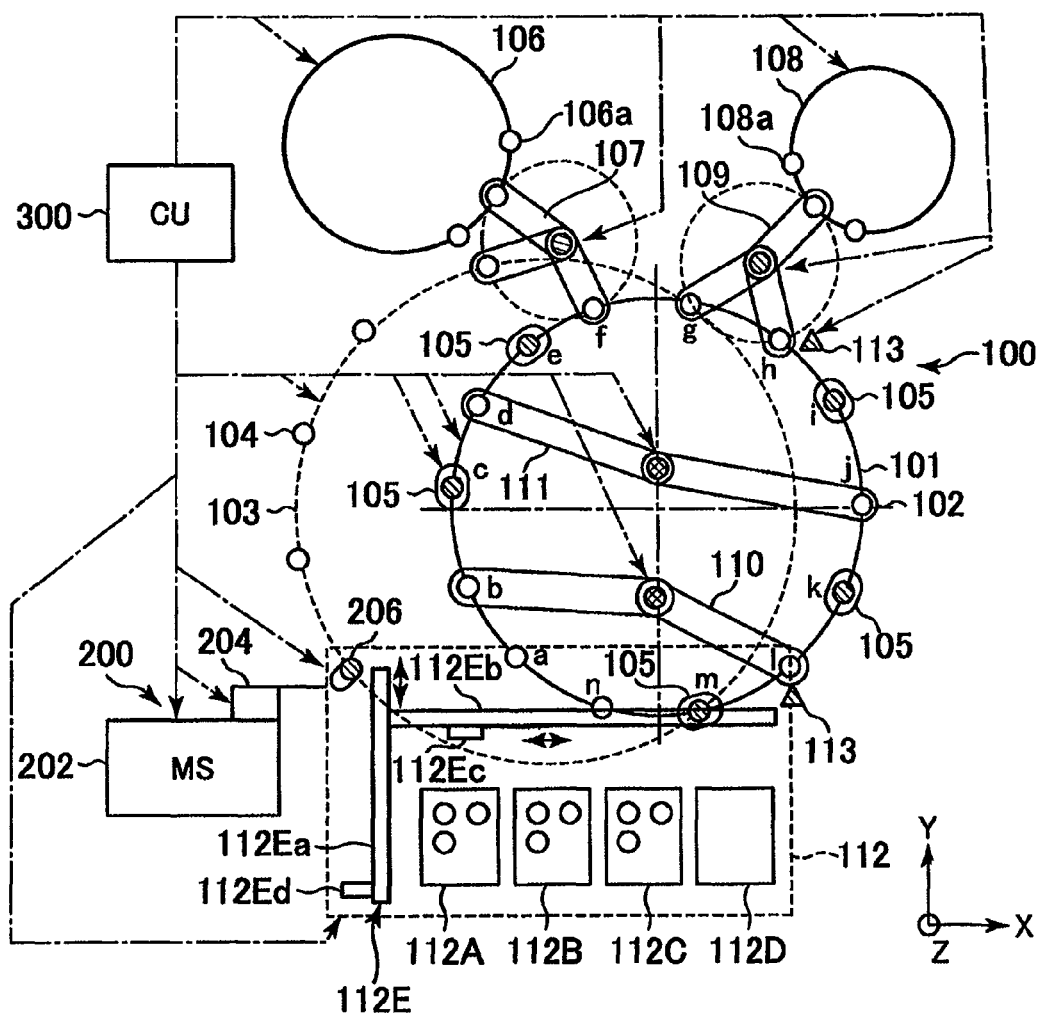
FIG. 1 is a plan view of the entire configuration of an examination device according to an embodiment of the present invention.

FIG. 1 is a plan view showing the entire configuration of the examination device according to the embodiment of the present invention. FIG. 2 is a perspective view showing the configuration of the main parts of the examination device according to the embodiment of the present invention. In FIGS. 1 and 2, the same reference numerals indicate the same parts.

The examination device illustrated in FIG. 1 according to this embodiment is an examination device for blood components. The device includes a pretreatment unit 100 for pretreating whole blood and serum/blood plasma, a mass analysis unit 200 for performing mass spectrometry on samples subjected to the pretreatment, and a controller 300. In this embodiment, pretreatment refers to processes performed before the sample is introduced into the mass analysis unit, or each element of those processes.

First, the configuration of the pretreatment unit 100 is described. The pretreatment unit 100 includes a cartridge table 101, a cup table 103, five pressure applying units 105, a sample disk 106, a sample probe 107, a reagent disk 108, a reagent probe 109, a methanol dispenser 110, a water dispenser 111, a consumable item rack 112, and two stirring mechanisms 113.

The mass analysis unit 200 includes a mass analyzer 202, an ionizing unit 204 and a pretreated sample introducing mechanism 206.

The controller 300 controls each of the components of the pretreatment unit 100 and mass analysis unit 200.

The cartridge table 101 can hold 14 solid-phase extraction cartridges 102 on a continuous track. The cartridge table 101 rotates at a constant pitch along the continuous track to transport the solid-phase extraction cartridges 102 to positions at which processes are performed so that they can be pretreated efficiently. In this example, the cartridge table 101 is circular and rotates approximately 26 degrees (=360/14 degrees) clockwise per 20 seconds. After rotating approximately 26 degrees, the cartridge table 101 stops for a while, and after elapse of 20 seconds, the cartridge table 101 rotates approximately 26 degrees again. The cartridge table 101 repeats this operation.

As described later, in the first half of a pretreatment for whole blood, i.e., the filtering process (hemolysis and deproteinization process), filters are set at the positions on the cartridge table 101 instead of the solid-phase extraction cartridges 102.

The number of solid-phase extraction cartridges 102 that can be set on the cartridge table 101 is not limited to 14. When the number is reduced, the area of the device can be reduced, but the throughput decreases. When the number is increased, the area of the device will be increased, but interference between operations of component devices can be reduced. Intervals between solid-phase extraction cartridges are constant in this embodiment. However, the intervals may be inconstant. In such case, the rotational speed of the cartridge table 101 is to be adjusted.

The solid-phase extraction cartridge 102 is a small container mini-column or cartridge filled with solid-phase beads or a membranous solid-phase extractant. A solid-phase extraction is a method for separating, purifying, and concentrating the examination target substance. The substance to be examined is sent through a solid-phase extraction cartridge to temporarily hold the substance in the solid-phase, and the solid-phase is then washed to collect the substance therefrom.

The filter used in the filtering process in the first half of the pretreatment process for whole blood is a cartridge having a filter for removing substances such as protein.

The pressure applying units 105 are placed above the five positions "c", "e", "i", "k", and "m" of the cartridge table 101. The pressure applying units 105 each adheres to the upper portion of a solid-phase extraction cartridge 102 to apply pressure. As described later referring to FIG. 12, the pressure applying units 105 apply pressure by compressing air like a syringe. However, the pressure applying units 105 may be a hydraulic type that compresses liquid. In the filtering process performed in the first half of the pretreatment for whole blood, the pressure applying units 105 each adheres to the upper portion of a filter set on the cartridge table 101 to apply pressure.

In the pretreatment for serum/blood plasma and the second half of the pretreatment of whole blood, pressurization is executed at the positions "c", "e", "i", "k", and "m" on the cartridge table 101. On the other hand, in the filtering process performed in the first half of the pretreatment for whole blood, pressurization is executed only at the position "m" on the cartridge table 101.

The cup table 103 is located below the cartridge table 101, and is capable of holding a plurality of cups 104 on a continuous track. The cup table 103 rotates clockwise. The rotational center of the cup table 103 is different from that of the cartridge table 101.

When viewed from above, the continuous track of the cup table 103 crosses the position "m" of the cartridge table 101 and a position at which the sample probe 107 operates. That is, the position "x" of the cup table 103 exists under the position "m" of the cartridge table 101. The position "z" of the cup table 103 is the position where the sample probe 107 operates. The position "y" of the cup table 103 is the position where the pretreated sample introducing mechanism 206 operates.

Thus, in the pretreatment for serum/blood plasma and the solid-phase extraction process of the second half of the pretreatment for whole blood, the eluate of the sample extracted from the solid-phase extraction cartridge 102 is received by a cup 104 at the position "m" on the cartridge table 101. In the filtering process of the first half of the pretreatment for whole blood, the eluate filtered through the filter at the position "m" of the cartridge table 101 is received by a cup 104.

The extracted eluate contained in the cup 104 is introduced into the mass analysis unit 200 by the pretreated sample introducing mechanism 206 at the position "y" on the cup table 103. On the other hand, the filtered eluate obtained by filtering contained in the cup 104 is sampled by the sample probe 107 at the position "z" on the cup table 103.

The cup table 103 and the cartridge table 101 do not need to have the same shape and rotational axis as described above. Since the cup table 103 and the cartridge table 101 are configured to cross each other, a space is provided above the cup table 103, which allows the cartridge table 101 not to interfere the sample aspiration from the cup 104 by the sample probe 107.

A plurality of sample containers 106a are set on the sample disk 106. The sample containers 106a contain whole blood or serum/blood plasma as samples to be examined.

The sample probe 107 aspirates a sample from the sample container 106a set on the sample disk 106 and dispenses the sample into a solid-phase extraction cartridge 102 or a filter at the position "f" on the cartridge table 101. When the sample is serum/blood plasma, the aspirated sample is dispensed into a solid-phase extraction cartridge 102 at the position "f" on the cartridge table 101. When the sample is whole blood, the aspirated sample is dispensed into a filter at the position "f" of the cartridge table 101.

In addition, the sample probe 107 aspirates the eluate obtained by filtering in the pretreatment for whole blood from the cup 104 on the cup table 103 and dispenses it into a solid-phase extraction cartridge 102 on the cartridge table 101.

As described above, the motion range of the sample probe 107 crosses a point on the circumference of the sample disk 106 and the position "f" of the cartridge table 101. The range also crosses the continuous track of the cup table 103 at the position "z". The sample probe 107 moves along an arc line and is also capable of moving vertically along Z axis. The configuration of the sample probe 107 is described later with reference to FIG. 2. In this embodiment, the sample disk 106 is of a disk type which can store a plurality of samples on a continuous track. However, the sample disk 106 may be a type such that racks capable of holding multiple samples are continuously transferred.

A plurality of reagent containers 108a are set on the reagent disk 108. The reagent containers 108a contain internal standard substances corresponding to a plurality of substances to be examined, diluting fluid used in the pretreatment of serum/blood plasma, and zinc sulfate aqueous solution used in the filtering process in the first half of the pretreatment for whole blood. Note that, in devices such as drug examination devices, internal standard substances are treated as a kind of reagent as well. Standard samples having different concentration of target substances, used to create a calibration curve, may also be set on the reagent disk 108.

The reagent probe 109 aspirates a reagent stored in the reagent disk 108 and adds it to a solid-phase extraction cartridge 102 or filter on the cartridge disk 101. The motion range of the reagent probe 109 crosses the positions "g" and "h" on the cartridge table 101. The reagent probe 109 adds an internal standard substance to the solid-phase extraction cartridge 102 at the position "g" of the cartridge table 101. The reagent probe 109 adds the diluting fluid for the pretreatment of serum/blood plasma at the position "h" on the cartridge table 101. The reagent probe 109 adds the zinc sulfate aqueous solution at the position "h" on the cartridge table 101 for the filtering process in the first half of the pretreatment for whole blood.

Since the diluting fluid is water, it may be supplied from the water dispenser 111. The zinc sulfate aqueous solution may be supplied from an independent dispenser. When the zinc sulfate aqueous solution is supplied using a dispenser, the reagent disk 108 can be downsized to allow the device to become even more compact.

The methanol dispenser 110 has a tank filled with methanol. The methanol dispenser 110 supplies methanol to solid-phase extraction cartridges 102 at the positions "b" and "l" on the cartridge table 101. In this embodiment, the methanol dispenser 110 is arranged inside the cartridge table 101 and the distances from its shaft to the positions "b" and "l" are equal. Alternatively, two independent methanol dispensers 110 may be disposed outside the cartridge table 101.

The water dispenser 111 has a tank filled with water. The water dispenser 111 supplies water to solid-phase extraction cartridges 102 at the positions "d" and "j" on the cartridge table 101. In this embodiment, the water dispenser 111 is arranged inside the cartridge table 101 and the distances from its shaft to the position "d" and position "j" are equal. Alternatively, two independent water dispensers 111 may be disposed outside the cartridge table 101.

The stirring mechanisms 113 stir solutions stored in solid-phase extraction cartridges 102 and filters at the positions "h and "l" on the cartridge table 101. The stirring mechanisms 113 in this embodiment use a stir bar to stir the solutions. The stirring mechanisms 113 are described in details later with reference to FIG. 11. Incidentally, the stirring mechanisms 113 may be a type that stirs solution by ultrasonic waves, or a type that stirs solution by rotating the stir bar by ultrasonic waves, or a type that vibrates the solid-phase extraction cartridge to thereby stir the solution.

In the pretreatment of serum/blood plasma and the second half of the pretreatment of whole blood, a solution stored in a solid-phase extraction cartridge 102 is stirred at the position "h" on the cartridge table 101. In the filtering process in the first half of the pretreatment for whole blood, a solution stored in a filter is stirred at the positions "h" and "l" on the cartridge table 101.

The consumable item rack 112 includes a rack 112A for storing solid-phase extraction cartridges 102; a rack 112B for storing cups 104; a rack 112C for storing filters 117; a waste box 112D for discarding used solid-phase extraction cartridges 102, cups 104, and filters 117; and a transport mechanism 112E for transporting a solid-phase extraction cartridge 102, a cup 104, and a filter 117.

The transport mechanism 112E includes a Y axis arm 112Ea, an X axis arm 112Eb, a handling unit 112Ec, and a power source 112Ed. The X axis arm 112Eb can be moved in the Y axis direction with respect to the Y axis arm 112Ea using the power of the power source 112Ed. The handling unit 112Ec is attached to the X axis arm and can be moved in the X axis direction and Z axis direction.

In the filtering process in the first half of the pretreatment for whole blood, the handling unit 112Ec transports a filter stored in the rack 112C to the position "a" on the cartridge table 101 and sets the filter thereat. The handling unit 112Ec transports a used filter from the position "n" on the cartridge table 101 to the waste box 112D and discards it.

In the pretreatment of serum/blood plasma and the second half of the pretreatment of whole blood, the handling unit 112Ec transports a solid-phase extraction cartridge 102 stored in the rack 112A to the position "a" of the cartridge table 101 and sets it at the position "a". The handling unit 112Ec transports a used solid-phase extraction cartridge 102 to the waste box 112D from the position "n" of the cartridge table 101 and discards it.

In addition, the handling unit 112Ec transports a cup 104 stored in the rack 112B to the position "x" of the cup table 103 and sets the cup 104 thereat. The handling unit 112Ec transports a used cup to the waste box 112D and discards it. The timing of transporting, setting, and discarding a solid-phase extraction cartridge 102, a cup 104, and a filter 117 is controlled by the controller 300 such that those steps are performed regularly during the series of processes of the pretreatment on the solid-phase extraction cartridge 102.

Figure 2:
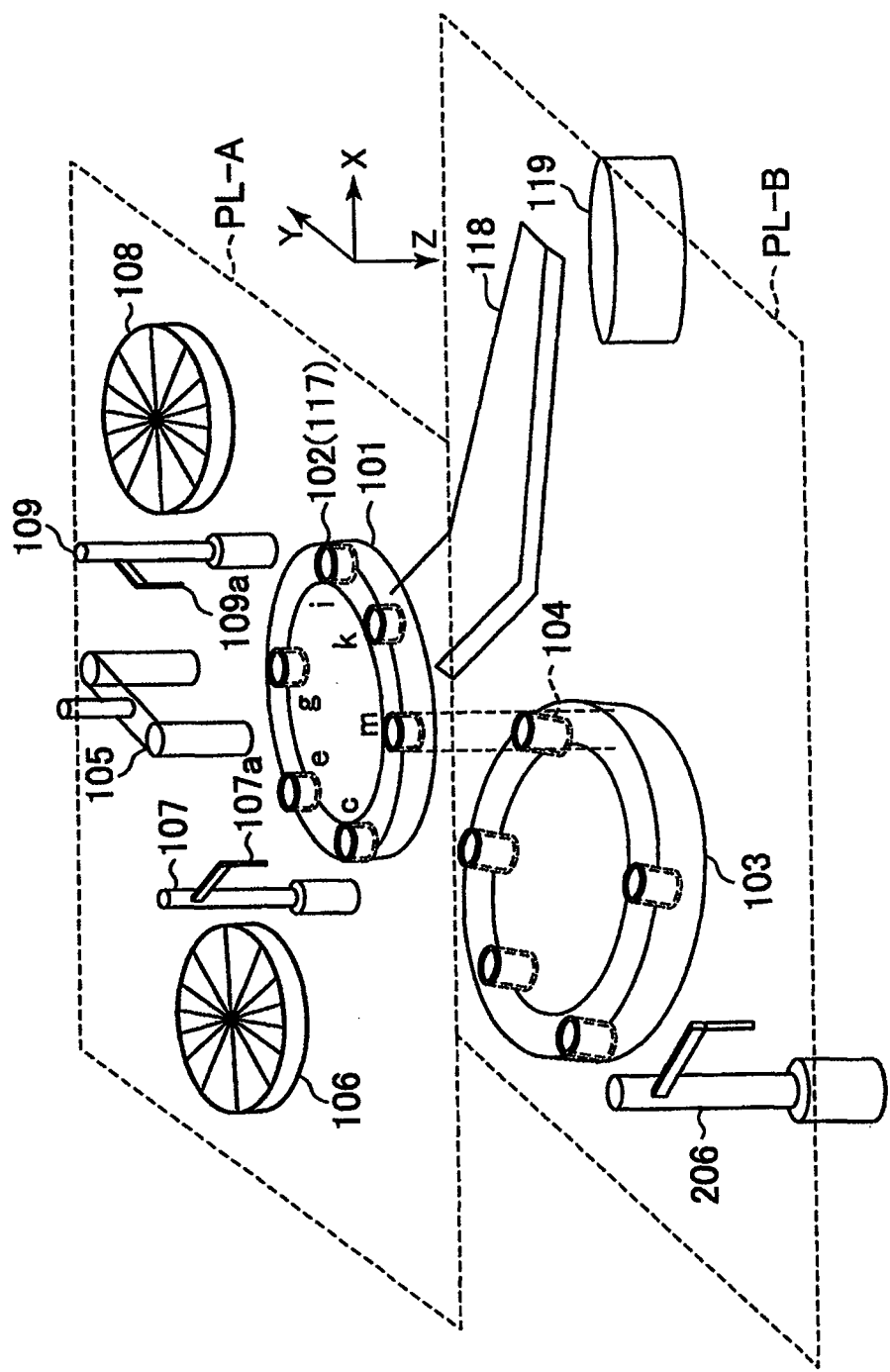
FIG. 2 is a perspective view of the configuration of the main parts of the examination device according to the embodiment of the present invention.

As illustrated in FIG. 2, the plane PL-A and the plane PL-B are planes existing on X-Y axes, and the two planes are separated from each other in the Z axial direction. The plane PL-B exists below the plane PL-A. The upper surfaces of the cartridge table 101, sample table 106 and reagent table 108 exist in the plane PL-A. The upper surface of the cup table 103 exists in the plane PL-B.

The position "x" of the cup table 103 is located under the position "m" of the cartridge table 101.

As illustrated in FIG. 1, the pressure applying units 105 are placed above the positions "c", "e", "i", "k", and "m" of the cartridge table 101. Referring to FIG. 2, a receiver 118 is placed under the position "k", for example. When pressure is applied by the pressure applying unit 105 from the upper portion of a solid-phase extraction cartridge 102 or a filter, the receiver 118 receives the waste liquid from the lower portion of the solid-phase extraction cartridge 102 or the filter. Then, the waste liquid is discarded into a waste liquid tank 119. Receivers 118 are also arranged under the positions "c", "e", "i", and "m" of the cartridge table 101 to discard the waste liquid into the waste liquid tank 119.

The sample probe 107 has a probe 107a at its end. The probe 107a is able to pivot in a plane parallel to the plane PL-A and can reciprocate in the Z axis direction. The end of the probe 107a is inserted into a sample contained in a sample container 106a or an eluate stored in a cup 104. The syringe is operated in one direction so that a certain amount of the sample or eluate is aspirated into the probe. After that, the probe moves to the position "f" on the cartridge table 101, and is inserted into the solid-phase extraction cartridge 102 or the filter on the cartridge table 101. The syringe is operated in the opposite direction so that the probe dispenses the sample or eluate.

The reagent probe 109 has a probe 109a at its end. The probe 109a is able to pivot in a plane parallel to the plane PL-A and can reciprocate in the Z axis direction. The end of the probe 109a is inserted into a reagent contained in a reagent container 108a. The syringe is operated in one direction so that a certain amount of the reagent is aspirated into the probe. After that, the probe moves to the position "g" or "h" of the cartridge table 101 and is inserted into the solid-phase extraction cartridge 102 or the filter on the cartridge table 101. The syringe is operated in the opposite direction so that the probe dispenses the reagent.

Next, the mass analysis unit 200 is described.

The mass analyzer 202 performs mass spectrometry on a target substance. In this embodiment, a triple quadrupole mass analyzer is used as the mass analyzer. The mass analyzer may instead be a quadrupole mass analyzer, an ion trap mass analyzer, a time-of-flight mass analyzer, or a Fourier transform ion cyclotron resonance mass analyzer. MS/MS including two MS in combination may be used as well. Incidentally, a high performance liquid chromatogram (HPLC), an ultra-high performance liquid chromatogram, gas chromatography, or capillary electrophoresis may also be employed.

The ionizing unit 204 applies voltage to a sample to ionize the sample. Samples are supplied to the ionizing unit 204 in a liquid state. As the ionizing unit 204, an ionizing unit used for LC-MS can be adopted.

The pretreated sample introducing mechanism 206 is located on the continuous track of the cup table 103. The pretreated sample introducing mechanism 206 aspirates a sample subjected to the pretreatment for serum/blood plasma or whole blood from a cup 104 at the position "y" and introduces the sample into the ionizing unit 204. The pretreated sample introducing mechanism 206 is such that a pump pushes out a liquid into which the liquid aspirated from the cup 104 is introduced. An autosampler mechanism can be applied.

The controller 300 controls the rotation of the cartridge table 101, rotation of the cup table 103, pressure application of the pressure applying units 105, rotation of the sample disk 106, operation of aspirating and dispensing a sample of the sample probe 107, rotation of the reagent disk 108, operation of aspirating and dispensing a reagent of the reagent probe 109, methanol supply operation of the methanol dispenser 110, water supply operation of the water dispenser 111, operation of supplying and discarding a solid-phase extraction cartridge 102 and other items of the consumable item rack 112, stir operation of the stirring mechanisms 113, analysis operation of the Mass analysis unit 200, ionization of the ionizing unit 204, and the sample introducing operation of the pretreated sample introducing mechanism 206.

Next, the pretreatment processes for serum/blood plasma and whole blood performed by the examination device according to this embodiment is described with reference to FIGS. 3 to 9.

First, the pretreatment for serum/blood plasma and whole blood by the examination device according to this embodiment is described with reference to FIG. 3.

FIG. 3 is a diagram showing the pretreatment processes for serum/blood plasma and whole blood performed by the examination device according to this embodiment.

An example of an examination item for which serum is used as a specimen is antiepileptic drugs, which may be phenytoin, valproic acid, carbamazepine, diazepam, phenobarbital, etc. In addition to antiepileptic drugs, items such as antifungal drugs, antimicrobial drugs, anti-asthma drugs, anti-HIV drugs, anticancer drugs, illicit drugs, etc. are examined. Examination items for which whole blood is used as a specimen are, for example, immunosuppressants used to suppress rejection to a transplanted organ, and more specifically, substances such as tacrolimus, cyclosporine, sirolimus, everolimus, etc.

In order to examine a very small amount of a target substance contained in a biological sample such as whole blood or serum/blood plasma, for example a drug, it needs to be purified and concentrated hence the amount of the component to be examined is very small. Employing solid-phase extraction to efficiently purify and concentrate the component allows more various types of substances to be examined in a small space and also the process speed can be increased.

The solid-extraction is a method of separating, purifying, and concentrating a target substance by temporarily holding the substance in a small container column or cartridge filled with solid-phase beads or a membranous solid-phase extractant and washing the solid-phase extraction cartridge to collect the target substance therefrom. The processes are: 1) a solid-phase conditioning process for passing an organic solvent through the solid-phase; 2) a solid-phase equilibration process for passing an aqueous medium through the solid-phase; 3) a process for passing the sample through the solid-phase so that the target substance is held in the solid-phase; 4) a washing process for passing water through the solid-phase; and 5) a process for passing an organic solvent through the solid-phase so as to elute the target substance from the solid-phase.

FIG. 3 shows the specific pretreatment processes performed for serum/blood plasma. The pretreatment is composed of processes 1 to 14: the process 1 for transporting a cartridge; process 2 for adding methanol; process 3 for applying pressure; process 4 for adding water; process 5 for applying pressure; process 6 for adding a sample; process 7 for adding an internal standard substance; process 8 for adding and stirring diluting fluid; process 9 for applying pressure; process 10 for adding water; process 11 for applying pressure; process 12 for adding methanol; process 13 for applying pressure; and process 14 for discarding the cartridge.

In cases where whole blood is used, the target substance is localized in blood cells. Thus, in the first half of the solid-extraction process, it is necessary to carry out a hemolytic process and a filtering process for aggregating, precipitating, and removing protein components by performing a deproteinization operation. The hemolytic process is done by causing osmotic pressure by adding a zinc sulfate aqueous solution. After that, an organic solvent is added and filtration is carried out by centrifugal separation or filtering.

The pretreatment for whole blood includes the processes 1 to 7 in the filtering process in the first half, and the processes 8 to 19 in the solid-phase extraction process in the second half. More specifically, the process 1 for transporting a filter; process 2 for adding a sample; process 3 for adding an internal standard substance; process 4 for adding a zinc sulfate aqueous solution; process 5 for adding methanol; process 6 for applying pressure; process 7 for transporting the filter; process 8 for transporting a cartridge; process 9 for adding methanol; process 10 for applying pressure; process 11 for adding water; process 12 for applying pressure; process 13 for adding a sample; process 14 for applying pressure; process 15 for adding water; process 16 for applying pressure; process 17 for adding methanol; process 18 for applying pressure; and process 19 for discarding the cartridge.

The second half of the pretreatment for whole blood (the process 8 and processes thereafter), i.e., the solid-phase extraction process and the following process, is similar to the pretreatment for serum. The processes 7 and 8 of serum pretreatment are not performed in the second half of the pretreatment for whole blood (the process 8 and processes thereafter). The process 7 of serum pretreatment for adding an internal standard substance is executed in the process 3 in whole blood pretreatment.

In terms of pretreatment for whole blood, it is most effective to configure the device in such a manner that mechanisms for serum pretreatment that can be shared with whole blood pretreatment are shared, whereby the pretreatment for whole blood can be carried out without reducing the throughput of serum/blood plasma pretreatment. A further study was made based on this concept, and as a result, a device configuration was devised which completes the pretreatment for serum/blood plasma in one rotation of the cartridge table and the pretreatment for whole blood in two rotations of the cartridge table. To be more specific, the solid-phase extraction process which is performed in both whole blood and serum/blood plasma pretreatment is shared, and also the first half of the pretreatment for whole blood, i.e., the steps before the solid-phase extraction process, are conducted using the same mechanisms used in solid-phase extraction. The device configuration can be simplified, and in addition, the device can perform pretreatments for serum/blood plasma and whole blood while maintaining the throughput of the pretreatment for serum/blood as high as possible.

In terms of the ratio of the usage of whole blood and serum/blood plasma as a specimen, the actual circumstances are that the hospitals that administer immunosuppressants are generally such large hospitals in which transplant surgeries are performed, and immunosuppressants are not administered in most hospitals. In addition, even in the sites where immunosuppressants are administered, the number of the patients is relatively small compared with the number of the patients to which antifungal drugs, antimicrobial drugs, or antiepileptic drugs are administered. Regarding such user needs, the basic concept of this device is to be a device that improves the throughput of the pretreatment for serum/blood plasma as possible having a compact size.

Next, the pretreatment for serum/blood plasma performed by the examination device according to the embodiment is described with reference to FIGS. 4 and 5. A case where an antiepileptic drug (diazepam) which requires pretreatment for serum/blood plasma is examined is here described.

Figure 4:
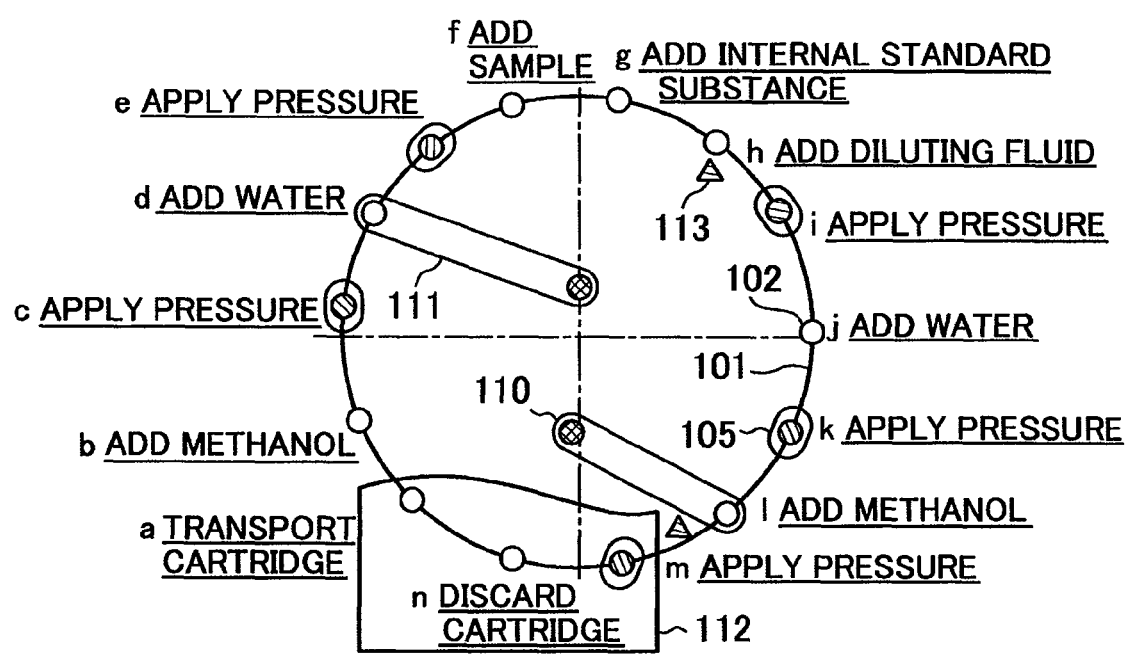
FIG. 4 is a diagram illustrating a rotation operation of a cartridge table in the pretreatment for serum/blood plasma performed by the examination device according to the embodiment of the present invention.
Figure 5:
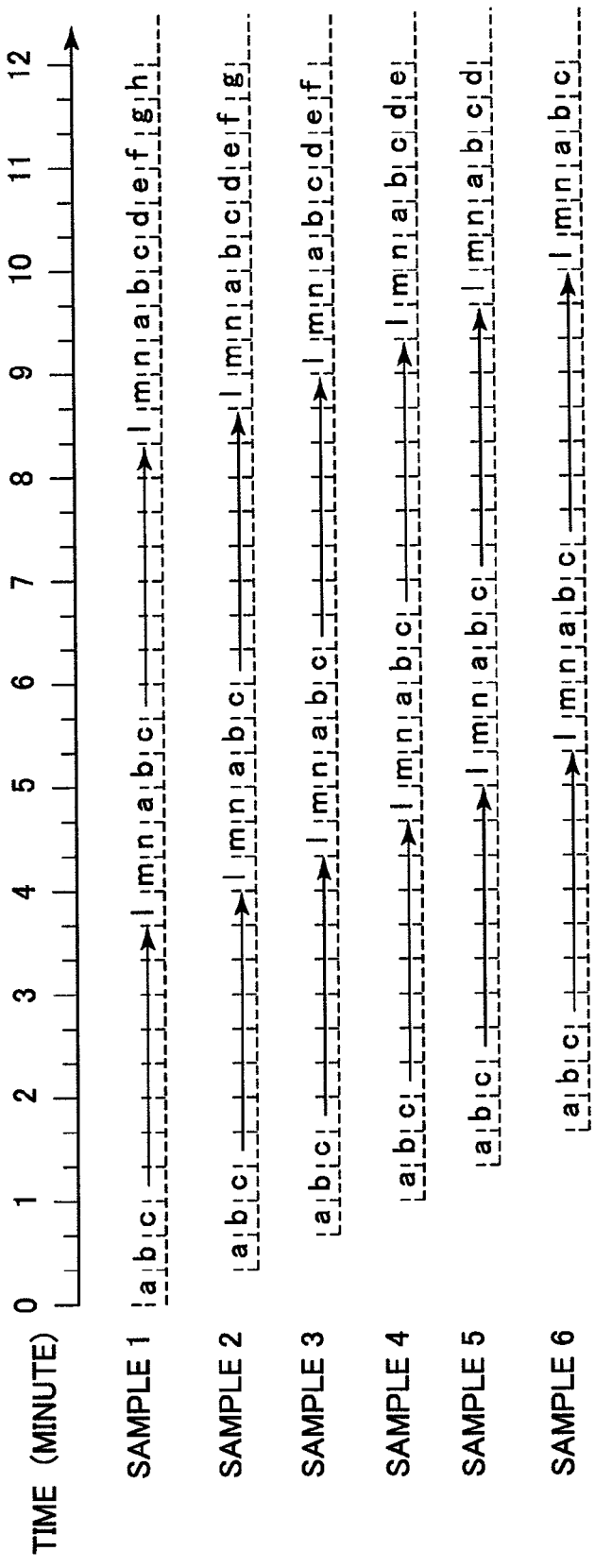
FIG. 5 is a diagram illustrating a basic cycle of the pretreatment for serum/blood plasma performed by the examination device according to the embodiment of the present invention.

FIG. 4 is a drawing describing the rotation operation of the cartridge table in the pretreatment for serum/blood plasma performed by the examination device according to the embodiment of the present invention. FIG. 5 is a diagram depicting the basic cycle of the pretreatment for serum/blood plasma performed by the examination device according to the embodiment of the present invention.

The pretreatment of serum/blood plasma is solid-phase extraction. Solid-phase extraction includes five processes: 1) a solid-phase conditioning process for sending an organic solvent through the solid-phase; 2) a solid-phase equilibration process for sending an aqueous medium through the solid-phase; 3) a process for sending the sample through the solid-phase so that the target substance is held in the solid-phase; 4) a washing process for sending water through the solid-phase; and 5) a process for sending an organic solvent through the solid-phase so as to elute the target substance from the solid-phase.

First, the solid-phase conditioning process for sending an organic solvent through the solid-phase is described. A solid-phase extraction cartridge 102 is transported from the consumable item rack 112 to the position "a" on the cartridge table 101 and set at the position "a".

Then, the solid-phase extraction cartridge 102 on the cartridge table 101 rotates to the position "b". The methanol dispenser 110 adds 200 μL of methanol to the solid-phase extraction cartridge 102.

Then, the solid-phase extraction cartridge 102 on the cartridge table 101 rotates to the position "c". The pressure applying unit 105 adheres to the upper portion of the solid-phase extraction cartridge 102 and applies pressure, whereby the methanol passes through the solid-phase extraction cartridge 102 to complete solid-phase conditioning process. Eluted methanol, i.e., the waste liquid drops on the receivers 118 disposed below the solid-phase extraction cartridges 102 for receiving the eluates from the positions "c", "e", "i", and "k". The receiver 118 is inclined with respect to a horizontal direction and configured so that the eluate naturally flows into the waste liquid tank 119.

Next, the solid-phase equilibration process for passing an aqueous medium through the solid-phase is described. The solid-phase extraction cartridge 102 on the cartridge table 101 rotates to the position "d". 200 μL of water is added from the water dispenser 111 to the solid-phase extraction cartridge 102.

Then, the solid-phase extraction cartridge 102 on the cartridge table 101 rotates to the position "e". The pressure applying unit 105 adheres to the upper portion of the solid-phase extraction cartridge 102 and applies pressure, whereby the water passes through the solid-phase extraction cartridge 102 to complete the solid-phase equilibration process.

Next, the process of passing a sample through the solid-phase to retain the target substance in the solid-phase is described. The sample is aspirated from the sample disk 106 by the sample probe 107 in synchronization with the rotation of the solid-phase extraction cartridge 102 on the cartridge table 101 to the position "f", and then dispensed into the solid-phase extraction cartridge 102 at the position "f". In this embodiment, serum of a patient to which 90 µL of diazepam was administered is added to the solid-phase extraction cartridge 102. The sample probe 107 is cleaned as appropriate at a cleaning port not shown after the aspiration and dispensation.

An internal standard solution is aspirated from the reagent disk 108 by the reagent probe 109 in synchronization with the rotation of the solid-phase extraction cartridge 102 on the cartridge table 101 to the position "g", and then dispensed into the solid-phase extraction cartridge 102 at the position "g". In this embodiment, the internal standard solution is a solution containing 10 µL of internal standard substance solution for diazepam, desmethyl diazepam, added with a methanol solution so that the concentration of desmethyl diazepam becomes 5000 ng/mL. The reagent probe 109 is cleaned as appropriate at a cleaning port not shown after the aspiration and dispensation.

Then, a diluting fluid is aspirated from the reagent disk 108 by the reagent probe 109 in synchronization with the rotation of the solid-phase extraction cartridge 102 on the cartridge table 101 to the position "h", and dispensed into the solid-phase extraction cartridge 102 at the position "h". In this embodiment, water is used as the diluting fluid, and 100 µL of the diluting fluid is added to the solid-phase extraction cartridge 102. After that, the stirring mechanism 113 stirs the sample, the internal standard substance, and the diluting fluid in the solid-phase extraction cartridge 102. The stirring mechanism 113 is cleaned as appropriate at a cleaning port not shown after the stirring.

The solid-phase extraction cartridge 102 on the cartridge table 101 rotates to the position "i". The pressure applying unit 105 adheres to the upper portion of the solid-phase extraction cartridge 102 and applies pressure, whereby the solution containing the sample passes through the solid-phase extraction cartridge 102. The process of retaining the target substance in the solid-phase is thus completed.

In this embodiment, diluting fluid is added. However, when the therapeutic range of the target substance is low and diluting is not required, diluting fluid does not need to be added at the position "h".

Next, the washing process for passing water through the solid-phase is described. 100 µL of water is added from the water dispenser 111 to the solid-phase extraction cartridge 102 in synchronization with the rotation of the solid-phase extraction cartridge 102 on the cartridge table 101 to the position "j".

Then, the solid-phase extraction cartridge 102 on the cartridge table 101 rotates to the position "k". The pressure applying unit 105 adheres to the upper portion of the solid-phase extraction cartridge 102 and applies pressure, whereby the water passes through the solid-phase extraction cartridge 102 to complete the washing process.

Next, the process of passing an organic solvent through the solid-phase to elute the target substance from the solid-phase is described. 100 µL of methanol is added to the solid-phase extraction cartridge 102 from the methanol dispenser 110 in synchronization with the rotation of the solid-phase extraction cartridge 102 on the cartridge table 101 to the position "l".

A cup 104 is transported from the consumable item rack 112 to the position "x" of the cup table 103 and set thereat in synchronization with the rotation of the solid-phase extraction cartridge 102 on the cartridge table 101 to the position "m". After that, the pressure applying unit 105 adheres to the upper portion of the solid-phase extraction cartridge 102 and applies pressure. The sample passes through the solid-phase extraction cartridge 102 to be eluted into the cup 104.

Then, the solid-phase extraction cartridge 102 on the cartridge table 101 rotates to the position "n" and the cartridge 102 is discarded. The cup 104 on the cup table 101 rotates to the position "y" where the pretreated sample introducing mechanism 206 operates. The pretreated sample introducing mechanism 206 aspirates the sample subjected to the pretreatment (solid-phase extraction) and introduces the aspirated sample into the mass analyzer 202. Data of the diazepam and desmethyl diazepam obtained by mass spectrometry are analyzed by the controller 300 and the examination results are output.

The examination is performed in such flow as described above. The solid-phase extraction cartridges 102 set on the cartridge table 101 rotates to the next position at a constant time period. FIG. 5 shows an example of operations carried out in a basic cycle when the specimens are serum/blood plasma. As shown in the diagram, examinations are performed in parallel. In this embodiment, up to 14 samples can be processed in parallel, and the time interval of the rotation to the next position is set at 20 seconds. Thus, examination of one sample is completed in 4 minutes and 40 seconds (completed at the position "n" in FIG. 4). When 14 samples are processed in parallel, 168 samples can be examined in 1 hour (actually 1 hour and 20 seconds).

Next, the pretreatment for whole blood performed by the examination device according to this embodiment is described with reference to FIGS. 6A, 6B, and 7. A case where an immunosuppressant (tacrolimus) which requires the pretreatment for whole blood is examined is described here.

Figure 6A:
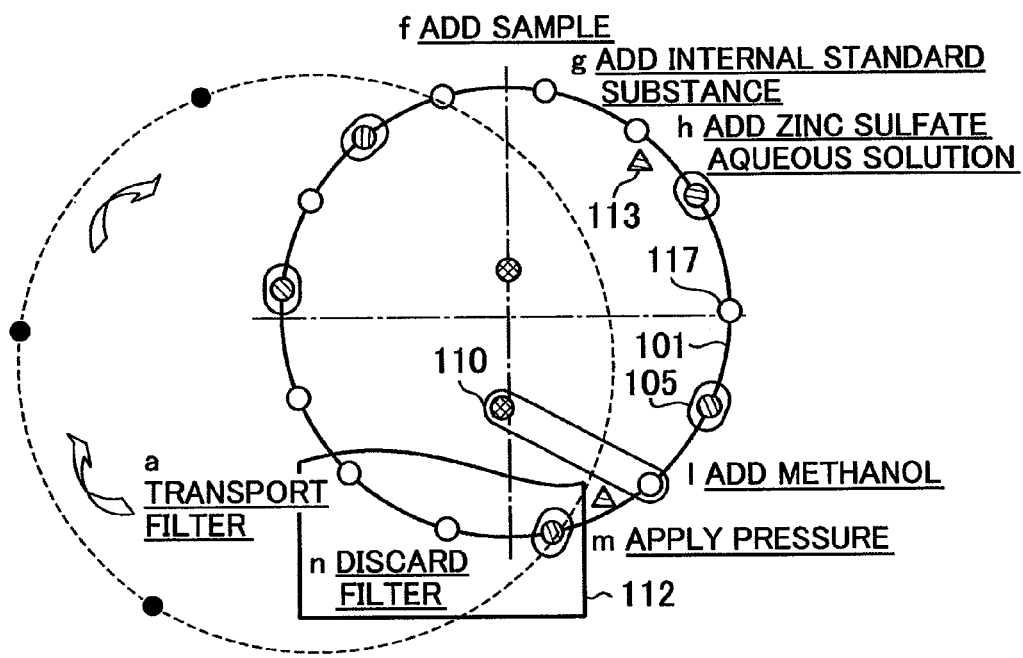
FIG. 6A is a diagram illustrating a rotation operation of the cartridge table in the pretreatment for whole blood performed by the examination device according to the embodiment of the present invention.
Figure 6B:
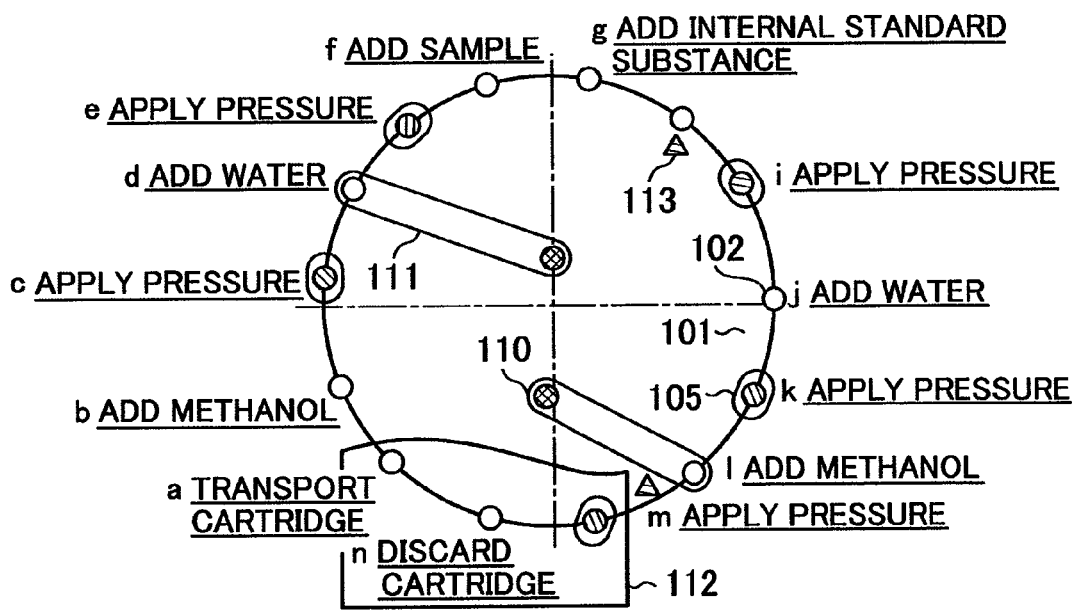
FIG. 6B is a diagram illustrating a rotation operation of the cartridge table in the pretreatment for whole blood performed by the examination device according to the embodiment of the present invention.
Figure 7:
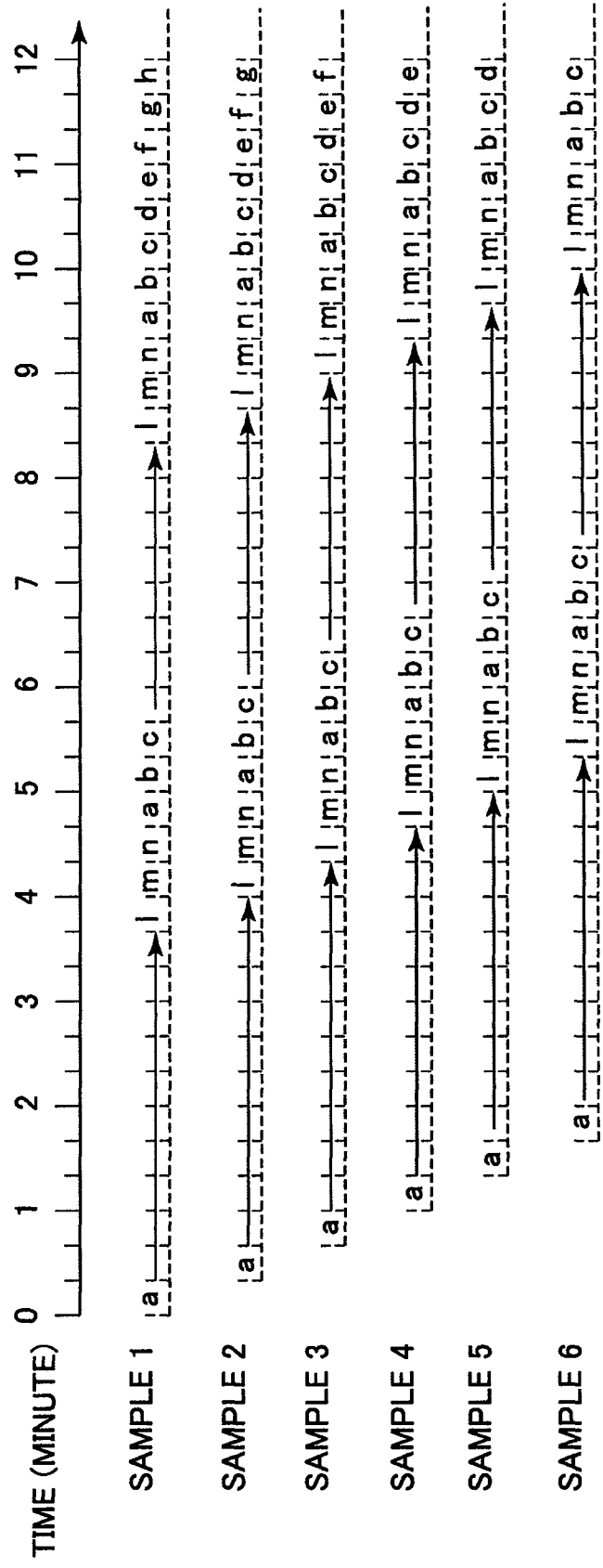
FIG. 7 is a diagram illustrating a basic cycle of the pretreatment for whole blood performed by the examination device according to the embodiment of the present invention.

FIGS. 6A and 6B are diagrams illustrating the rotation operation of the cartridge table in the pretreatment for whole blood performed by the examination device according to the embodiment of the present invention. FIG. 7 is a diagram illustrating the basic cycle of the pretreatment for whole blood performed by the examination device according to the embodiment of the present invention.

The pretreatment of whole blood is completed in two rotations of the cartridge table. FIG. 6A illustrates the first half of the pretreatment of whole blood which corresponds to the processes 1 to 7 shown in FIG. 3. FIG. 6B illustrates the second half of the pretreatment of whole blood which corresponds to the process 8 and processes thereafter. The solid-phase extraction process which is the second half of the pretreatment of whole blood (the process 8 and processes thereafter of the pretreatment of whole blood shown in FIG. 3) is almost the same to the pretreatment of serum/blood plasma. Thus, only the points different from FIG. 4 are described.

In the pretreatment for whole blood, a hemolysis process and a process for aggregating, precipitating, and removing protein components by a deproteinization operation need to be performed in the first half before solid-phase extraction. The hemolysis process and the deproteinization process are completed in one rotation of the cartridge table on which the filters are placed.

First, the hemolysis process is described. A filter 117 is transported from the consumable item rack 112 to the position "a" of the cartridge table 101 and set thereat.

Then, the filter 117 on the cartridge table 101 rotates to the position "b". The filter 117 subsequently moves to the positions "c", "d", and "e" at constant time intervals. Next, a sample is aspirated from the sample disk 106 by the sample probe 107 in synchronization with the rotation of the filter 117 on the cartridge table 101 to the position "f", where it is dispensed into the filter 117. In this embodiment, whole blood of a patient to which 90 μL of tacrolimus was administered is added into the filter 117. The sample probe 107 is cleaned as appropriate at a cleaning port not shown after the aspiration and dispensation.

Then, an internal standard solution is aspirated from the reagent disk 108 by the reagent probe 109 in synchronization with the rotation of the filter 117 on the cartridge table 101 to the position "g", and the solution is dispensed into the solid-phase extraction cartridge 102 located at the position "g". In this embodiment, the internal standard solution is a solution containing 10 μL of internal standard substance solution for tacrolimus, ascomycin, added with a methanol solution so that the concentration of ascomycin becomes 200 ng/mL. The reagent probe 109 is cleaned as appropriate at a cleaning port not shown after the aspiration and the dispensation.

Then, a zinc sulfate aqueous solution for hemolysis is aspirated from the reagent disk 108 by the reagent probe 109 in synchronization with the rotation of the filter 117 on the cartridge table 101 to the position "h", and it is dispensed into the filter 117 at the position "h". In this embodiment, 200 μL of 0.5M zinc sulfate aqueous solution is added to the filter 117. After that, the stirring mechanism 113 stirs the sample, the internal standard substance, and the diluting fluid in the filter 117. The stirring mechanism 113 is cleaned as appropriate at a cleaning port not shown after the stirring.

Then, the filter 117 on the cartridge table 101 moves to the positions "i", "j", and "k" at constant time intervals. Hemolysis is caused by osmotic pressure during this movement of the filter 117.

Next, the deproteinization process is described. 300 μL of methanol (organic solvent) is added to the filter 117 by the methanol dispenser 110 in synchronization with the rotation of the filter 117 on the cartridge table 101 to the position "i". After that, the stirring mechanism 113 stirs the sample, the internal standard substance, and the diluting fluid in the filter 117. The stirring mechanism 113 is cleaned as appropriate at a cleaning port not shown after the stirring.

Then, a cup 104 is transported from the consumable item rack 112 to the position "x" of the cup table 103 in synchronization with the rotation of the filter 117 on the cartridge table 101 to the position "m". After that, the pressure applying unit 105 adheres to the upper portion of the filter and applies pressure. The sample passes through the filter 117, and the filtered sample is eluted into the cup 104 below on the cup table 103.

Then, the filter 117 on the cartridge table 101 rotates to the position "n" and is discarded. The cup 104 on the cup table 103 rotates to the position "z" at which the sample probe 107 operates. The first half of the pretreatment for whole blood (processes 1 to 7 of the pretreatment for whole blood shown in FIG. 3) is thus completed in one rotation of the cartridge table.

Next, the second half of the pretreatment of whole blood is described (the process 8 and processes thereafter of the pretreatment of whole blood shown in FIG. 3). In the second half of the pretreatment of whole blood, the solid-phase extraction is performed as with the pretreatment of serum/blood plasma shown in FIG. 4. The difference between the solid-phase extraction processes of the two is in the sample adding at the position "f". The sample is aspirated by the sample probe 107 not from the sample disk 106 but from the cup 104 containing the filtered sample and is dispensed into the solid-phase extraction cartridge 102 at the position "f". The cup 104 moves along the continuous track of the cup table 103 to the position "n" and is discarded thereat. The motion range of the sample probe 107 crosses a point on the circumference of the sample disk 106, the position "f" of the cartridge table 101, and the continuous track of the cup table 103. Hence the sample from the cup table 103 needs to be carried to the cartridge table 101, the sample probe 107 is configured to move along an arc line and vertically along the Z-axis.

After that, pretreatment processes same as those shown in FIG. 4 are performed as the cartridge 102 moves through the positions "g" to "m". At the position "m", the sample passes through the solid-phase extraction cartridge 102 and the extracted sample is eluted into the cup 104.

Then, the solid-phase extraction cartridge 102 rotates to the position "n" and is discarded thereat. The cup 104 on the cup table 103 rotates to the position "y" at which the pretreated sample introducing mechanism 206 operates. The sample subjected to the pretreatment (solid-phase extraction) is aspirated from the cup 104 and introduced into the mass analyzer 202. Data of the tacrolimus and ascomycin obtained by mass spectrometry are analyzed by the controller 300, and the examination results are output.

The examination is performed through such flow described above. The solid-phase extraction cartridge 102 on the cartridge table 101 rotates to the next position at a constant time period. FIG. 7 illustrates an example of operations of a basic cycle of when the specimens are serum/blood plasma. As illustrated in FIG. 7, samples are examined in parallel. In this embodiment, up to 14 samples can be processed in parallel, and the time interval of the rotation to the next position is set at 20 seconds. Thus, examination of one sample is completed in 9 minutes and 20 seconds (completed at the position "n" illustrated in FIGS. 6A and 6B). When 14 samples are processed in parallel, 84 samples can be examined in 1 hour (actually 1 hour and 20 seconds).

Next, the pretreatment processes performed by the examination device according to the embodiment of the present invention, for cases where both whole blood and serum/blood plasma specimens are to be examined is described with reference to FIGS. 8A, 8B, 8C, 8D, and 9.

FIGS. 8A, 8B, 8C, and 8D are diagrams illustrating rotation operations of the cartridge table in the pretreatment by the examination device according to the embodiment of the present invention for cases where whole blood and serum/blood plasma specimens are both examined. FIG. 9 is a diagram illustrating the basic cycle of the pretreatment by the examination device according to the embodiment of the present invention for cases where whole blood and serum/blood plasma specimens are both examined.

Figure 8A:
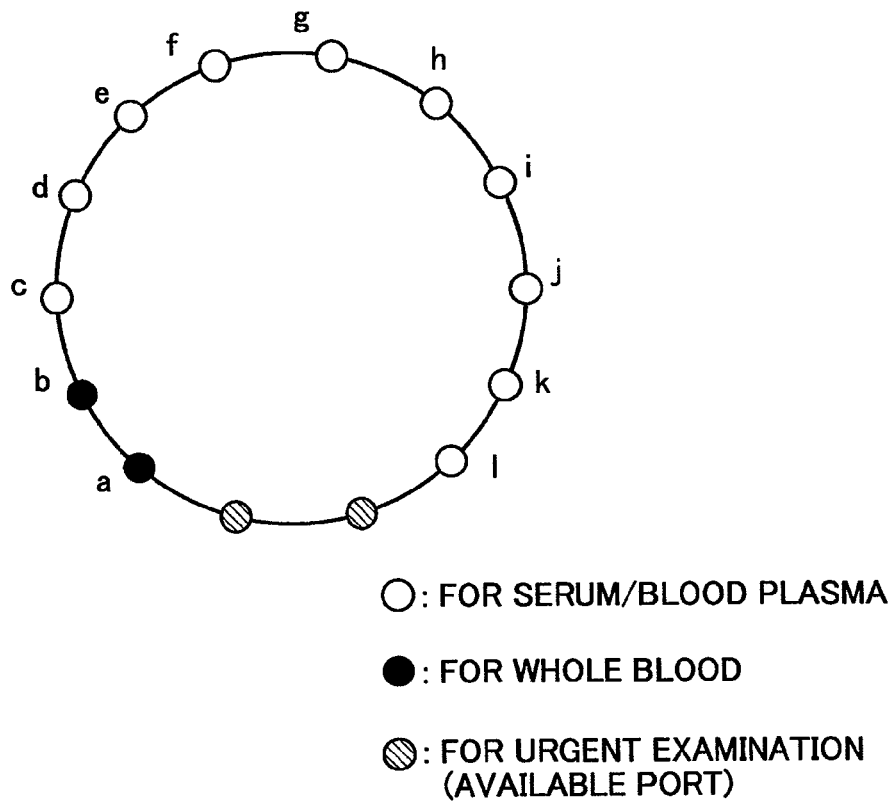
FIG. 8A is a diagram illustrating a rotation operation of the cartridge table in the pretreatment for serum/blood plasma and whole blood specimens performed by the examination device according to the embodiment of the present invention.
Figure 9:
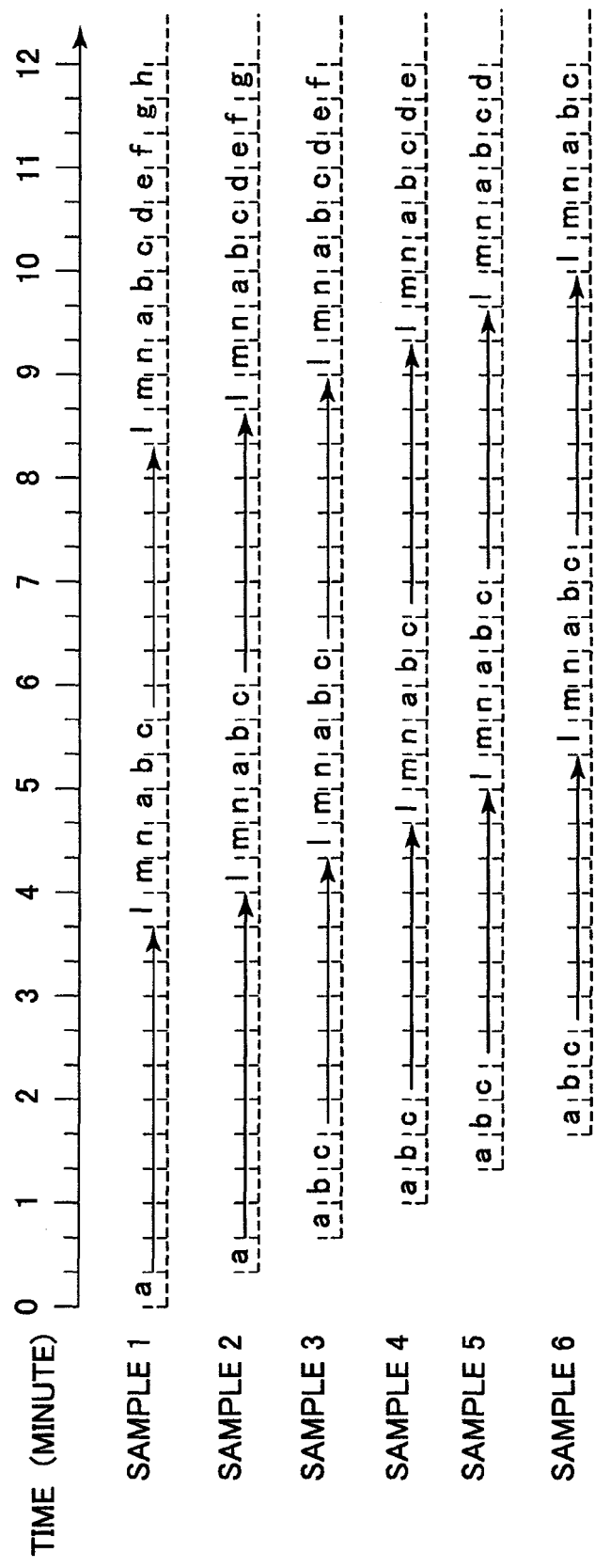
FIG. 9 is a diagram illustrating a basic cycle of the pretreatment for serum/blood plasma and whole blood specimens performed by the examination device according to the embodiment of the present invention.

FIG. 8A shows a case where the ratio of the throughput of the pretreatment for whole blood to that of serum/blood plasma is 1 to 10. In this case, the two ports represented by black circles are assigned to whole blood specimens, while the ten ports represented by white circles are assigned to serum/blood plasma specimens. The other two ports are ports for an urgent specimen and used to examine an urgent specimen as required. The pretreatment of the whole blood is completed in two rotations of the cartridge table 101, while the pretreatment of the serum/blood plasma is completed in one rotation of the cartridge table 101. Thus, the throughput of the pretreatment of a serum/blood plasma specimen is twice as high as that of a whole blood specimen.

As described above, in terms of the ratio of the usage of whole blood and serum/blood plasma as a specimen, the actual circumstances are that the hospitals that administer immunosuppressants are generally such large hospitals in which transplant surgeries are performed, and immunosuppressants are not administered in most hospitals. In addition, even in the sites where immunosuppressants are administered, the number of the patients is relatively small compared with the number of the patients to which antifungal drugs, antimicrobial drugs, or antiepileptic drugs are administered. When such is the case, as illustrated in FIG. 8A, the number of ports to be used for whole blood specimens is reduced so as to improve the throughput of the pretreatment for serum/blood plasma specimens.

As illustrated in FIG. 9, when the ports are assigned as in FIG. 8A, examination can be carried out even when both whole blood specimens (samples 1 and 2) and serum/blood plasma specimens (sample 3 and the rest) are to be examined. In this embodiment, two whole blood samples and ten serum/blood plasma samples are processed in parallel, and the time interval of the rotation to the next position is set at 20 seconds. Thus, 12 whole blood samples, 120 serum/blood plasma samples, and 12 urgent specimens can be examined in 1 hour (actually 1 hour and 20 seconds).

Figure 8B:
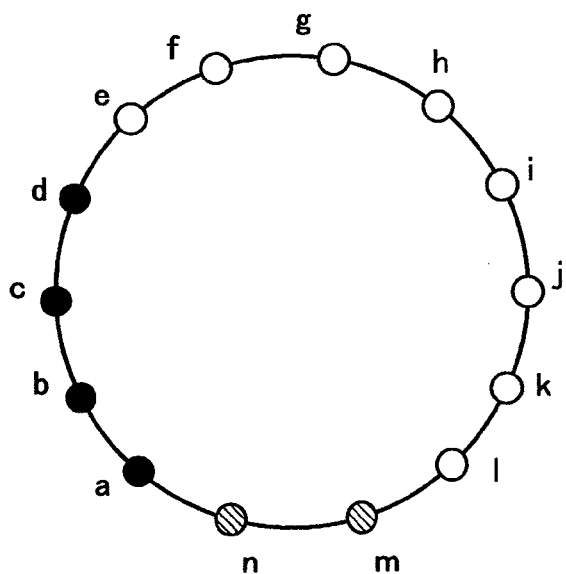
FIG. 8B is a diagram illustrating a rotation operation of the cartridge table in the pretreatment for serum/blood plasma and whole blood specimens performed by the examination device according to the embodiment of the present invention.

FIG. 8B illustrates a case where the ratio of the throughput of the pretreatment for whole blood specimens to that for serum/blood plasma specimens is 1 to 4. In this case, the four ports represented by black circles are assigned to whole blood specimens, while the eight ports represented by white circles are assigned to serum/blood plasma specimens. The other two ports are used for urgent specimens. In this example, 24 whole blood samples and 96 serum/blood plasma samples can be examined in 1 hour (actually 1 hour and 20 seconds).

Figure 8C:
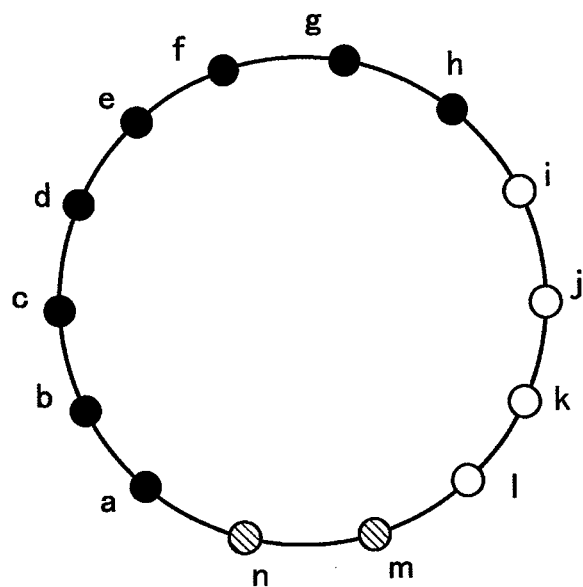
FIG. 8C is a diagram illustrating a rotation operation of the cartridge table in the pretreatment for serum/blood plasma and whole blood specimens performed by the examination device according to the embodiment of the present invention.

FIG. 8C illustrates a case in which the ratio of the throughput of the pretreatment for whole blood specimens to that for serum/blood plasma specimens is 1 to 1. In this case, the eight ports represented by black circles are assigned to whole blood specimens, while the four ports represented by white circles are assigned to serum/blood plasma specimens. The other two ports are used for urgent specimens. In this example, 48 whole blood samples and 48 serum/blood plasma samples can be examined in 1 hour (actually 1 hour and 20 seconds).

Figure 8D:
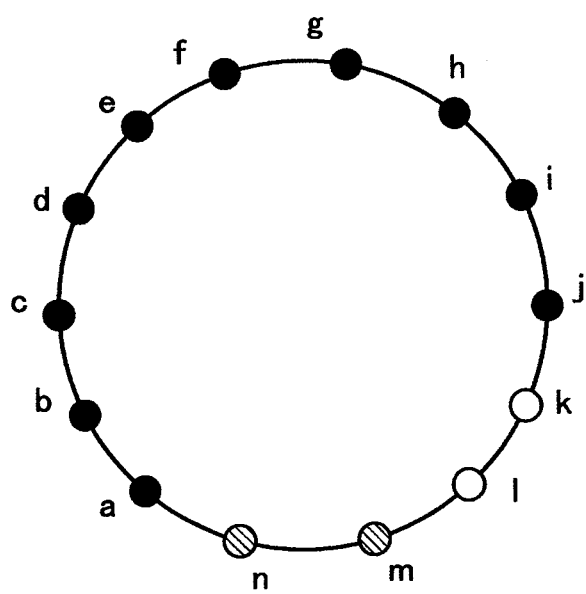
FIG. 8D is a diagram illustrating a rotation operation of the cartridge table in the pretreatment for serum/blood plasma and whole blood specimens performed by the examination device according to the embodiment of the present invention.

FIG. 8D illustrates a case in which the ratio of the throughput of the pretreatment for whole blood specimens to that for serum/blood plasma specimens is 5 to 2. In this case, the ten ports represented by black circles are assigned to whole blood specimens, while the two ports represented by white circles are assigned to serum/blood plasma specimens. The other two ports are used for urgent specimens. In this example, 60 whole blood samples and 24 serum/blood plasma samples can be examined in 1 hour (actually 1 hour and 20 seconds).

The ports can be flexibly assigned by the user according to the types of whole blood specimens and serum/blood plasma specimens the user handles including the ports for urgent specimens, which is convenient for the user.

In this embodiment, the time interval of the rotation of the cartridge table is set at 20 seconds. The processing time required for each of the processes performed in the rotation interval is set to be the same. This time is determined by the pressure applying process carried out by the pressure applying unit, which takes the longest time and is the rate-limiting factor. The throughput can be changed by changing the diameter of the filler of the solid-phase extraction or the mesh of the filter so that the resistance becomes low or high and thereby setting the rotation time interval shorter or longer.

An examination device according to this embodiment can efficiently and highly accurately examine whole blood and serum/blood plasma specimens with low cost while the device is kept compact in size. If the ports on the cartridge table 101 are assigned with priority to serum/blood plasma specimens, specimens can be examined without decreasing the throughput of the pretreatment for serum/blood plasma specimens.

Next, the configuration of the water dispenser 111 used in the examination device according to this embodiment is described with reference to FIG. 10.

Figure 10:
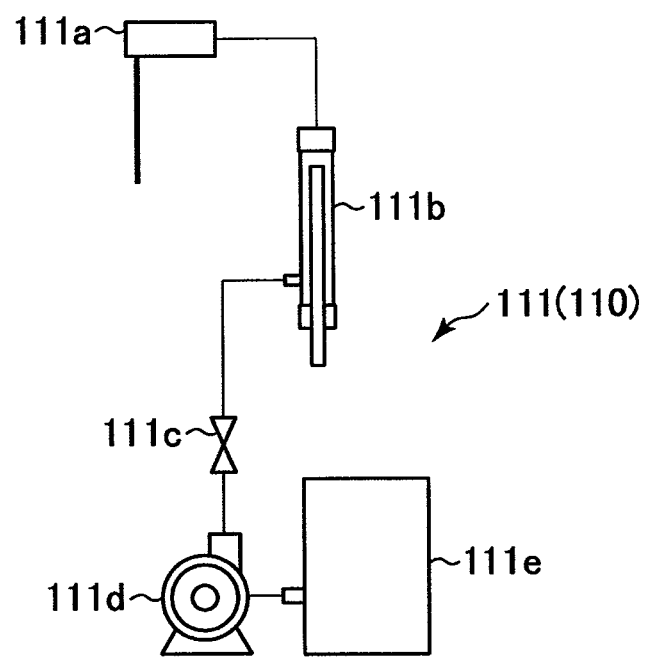
FIG. 10 is a block diagram illustrating a water dispenser used in the examination device according to the embodiment of the present invention.

FIG. 10 is a block diagram illustrating the configuration of the water dispenser 111 used in the examination device according to the embodiment of the present invention.

The water dispenser 111 includes a probe 111a, a syringe 111b, a water supply valve 111c, a pump 111d, and a storage tank 111e. The storage tank 111e contains water. The water stored in the storage tank 111e is supplied to the syringe 111b by the pump 111d. A plunger included in the syringe 111b is moved for a certain distance, whereby a certain amount of water can be dispensed from the end of the probe 111a.

The methanol dispenser 110 has the same configuration as the water dispenser 111. However, methanol is stored in the storage tank 111e.

Next, the configuration of the stirring mechanism 113 used in the examination device according to this embodiment is described with reference to FIG. 11.

Figure 11:
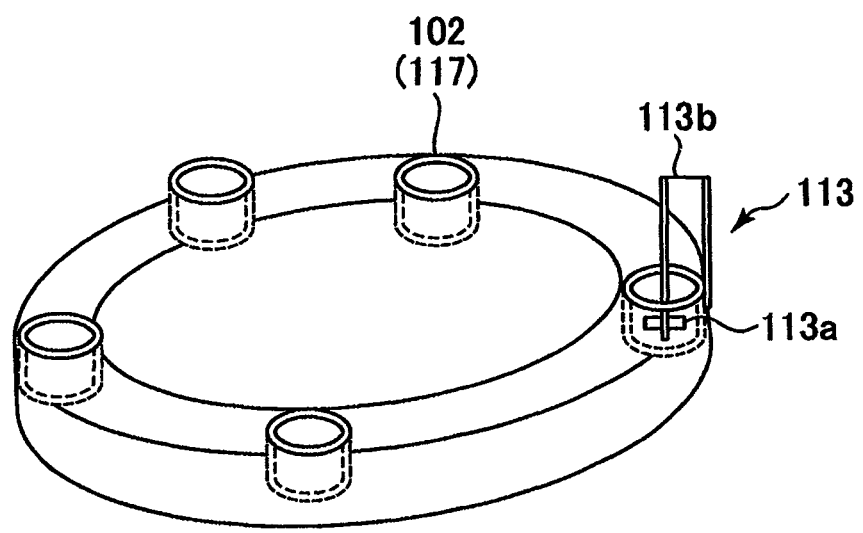
FIG. 11 is a block diagram illustrating a stirring mechanism used in the examination device according to the embodiment of the present invention.

FIG. 11 is a block diagram illustrating the configuration of the stirring mechanism used in the examination device according to this embodiment.

The stirring mechanism 113 inserts a stirring bar 113b equipped with a blade 113a at its end into a container such as a solid-phase extraction cartridge 102 and stirs the solution contained in the container by rotating the blade 113a.

Next, the configuration and operations of the pressure applying units 105 used in the examination device according to this embodiment are described with reference to FIG. 12.

Figure 12:
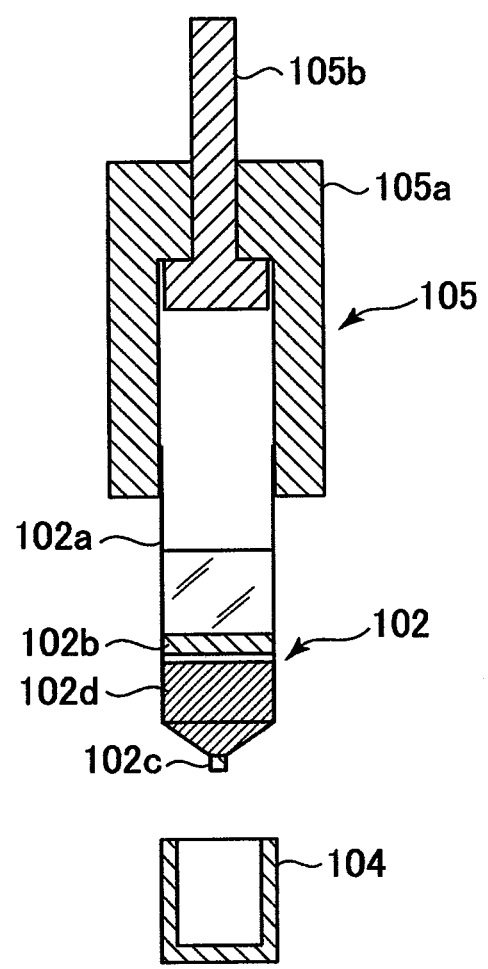
FIG. 12 is a block diagram illustrating a pressure applying unit used in the examination device according to the embodiment of the present invention.

FIG. 12 is a block diagram illustrating the configuration of the pressure applying units used in the examination device according to this embodiment.

The pressure applying units 105 include a pressure applying unit holder 105a and a pressurizing syringe 105b. The pressure applying unit holder 105a is attached to the solid-phase extraction cartridge 102 in such a manner that there is no gap between the pressure applying unit holder 105a and the upper portion of the solid-phase extraction cartridge 102.

The solid-phase extraction cartridges 102 include a cartridge body 102a, an upper filter 102b, a lower filter 102, and a solid-phase extractant 102b. The solid-phase extractant 102d is sandwiched between the upper filter 102b and the lower filter 102c and held inside the cartridge body 102a. As the solid-phase extractant 102d, a filler generally called a reversed-phase system can be used which adsorbs immunosuppressants contained in a blood sample solution by hydrophobic interaction. For example, microparticles formed by adding an octadecyl group onto the surface of organic polymer such as NOBIAS RP-OD1 made by Hitachi High-Technologies Corporation can be used. The upper filter 102b and the lower filter 102c have a mesh diameter of about 1.0 μm, for example.

The pressure applying syringe 105b is moved toward the solid-phase extraction cartridge 102 side (in the downward direction in FIG. 12) to compress the gas inside the solid-phase extraction cartridge 102 and increase the internal pressure. The solution passes through the filter 102c and is dispensed to the outside by the pressure applying.

The filter 117 used in the first half of the pretreatment for whole blood is constructed from the cartridge body 102a of the solid-phase extraction cartridge 102 and the filter 102c, and has the same external dimensions as those of the solid-phase extraction cartridge 102.

According to this embodiment, regarding a case where both whole blood specimens and serum/blood plasma specimens are examined by a clinical application of mass spectrometry, the elements of the application are arranged such that the pretreatment of serum/blood plasma specimens is completed in one rotation of the cartridge table and the pretreatment of whole blood specimens is completed in two rotations of the cartridge table. Thus, even when both whole blood and serum/blood plasma specimens are to be examined, the examination can be carried out efficiently, especially without decreasing the throughput of the pretreatment for serum/blood plasma specimens as possible with high accuracy and low cost while keeping the size of the device compact.

Thus, even when both whole blood and serum/blood plasma are used as specimens, it is possible to efficiently perform examinations with high accuracy and low cost without increasing the size of the device.

DESCRIPTION OF REFERENCE NUMERALS

101 ... Cartridge table
102 ... Solid-phase extraction cartridge
103 ... Cup table
104 ... Cup
105 ... Pressure applying unit
106 ... Sample disk
107 ... Sample probe
108 ... Reagent disk
109 ... Reagent probe
110 ... Methanol dispenser
111 ... Water dispenser
112 ... Consumable item rack
113 ... Stirring mechanism
117 ... Filter
200 ... Mass analysis unit
202 ... Mass analyzer
204 ... Ionizing unit
206 ... Pretreated sample introducing mechanism
300 ... Controller

The invention claimed is:

1. An examination device comprising:
    a cartridge table that can hold a solid-phase extraction cartridge and a filter on a continuous track;
    a plurality of pressure applying units arranged above the cartridge table, the pressure applying units applying pressure to the inside of the solid-phase extraction cartridge and the inside of the filter;
    a cup table disposed below the cartridge table, the cup table being able to hold on a continuous track a cup by which a purified sample is received;
    a sample probe for dispensing a sample into the solid-phase extraction cartridge and the filter;
    a reagent probe for dispensing a reagent into the solid-phase extraction cartridge and the filter; and
    an analyzer for analyzing an eluate obtained by completing a pretreatment;
    wherein a pretreatment of serum/blood plasma is completed in one rotation of the cartridge table, and a pretreatment of whole blood is completed in two rotations of the cartridge table.

2. The examination device according to claim 1, wherein:
    the continuous track of the cartridge table and the continuous track of the cup table cross each other at a first position when viewed from above;
    the continuous track of the cup table and a position at which the sample probe operates cross at a second position;
    the cup on the cup table receives the eluate eluted from the filter on the cartridge table at the first position;
    the sample probe aspirates the eluate from the cup at the second position; and
    the sample probe dispenses the eluate into a solid-phase extraction cartridge on the cartridge table.

3. The examination device according to claim 2, further comprising:
    a water dispenser for adding water to a liquid contained in a solid-phase extraction cartridge at a plurality of positions on the cartridge table;
    a methanol dispenser for adding methanol to a liquid contained in a solid-phase extraction cartridge at a plurality of positions on the cartridge table; and
    a reagent disk that holds a plurality of reagents, the reagent disk being disposed at a position where the reagent probe can operate;
    wherein in the pretreatment for serum/blood plasma, an internal standard substance held by the reagent disk is added into a solid-phase extraction cartridge on the cartridge table; and
    in the pretreatment for whole blood, an internal standard substance held by the reagent disk is added into a filter on the cartridge table.

4. The examination device according to claim 1, wherein a total of 14 solid-phase extraction cartridges and/or filters are set on the continuous track of the cartridge table.

5. The examination device according to claim 1, wherein each of the processes on the cartridge table is performed at constant time intervals.

6. The examination device according to claim 1, wherein:
    the rotational center of the cup table is located at a position different from the rotational center of the cartridge table; and
    the sample probe and a pretreated sample introducing mechanism can access from above the cup table.

* * * * *